United States Patent
Han

(10) Patent No.: US 8,354,391 B2
(45) Date of Patent: Jan. 15, 2013

(54) ANTI-WSSV AND/OR TSV NUCLEIC ACID DRUG

(75) Inventor: Jianbao Han, Jiangsu (CN)

(73) Assignee: Nanjing Sen Nan Biotechnology Research Co., Ltd, Nanjing (CN)

( * ) Notice: Subject to any disclaimer, the term of this patent is extended or adjusted under 35 U.S.C. 154(b) by 0 days.

(21) Appl. No.: 13/439,007

(22) Filed: Apr. 4, 2012

(65) Prior Publication Data

US 2012/0259003 A1 Oct. 11, 2012

Related U.S. Application Data

(63) Continuation of application No. PCT/CN2011/077087, filed on Jul. 12, 2011.

(30) Foreign Application Priority Data

Jul. 16, 2010 (CN) .......................... 2010 1 0228664

(51) Int. Cl.
*C12N 15/11* (2006.01)
(52) U.S. Cl. ..................................................... 514/44 A
(58) Field of Classification Search ........................ None
See application file for complete search history.

(56) References Cited

U.S. PATENT DOCUMENTS 6,908,616 B2 * 6/2005 Vlak et al. ................. 424/204.1

OTHER PUBLICATIONS

Lu, Y. et al., "Viral resistance in shrimp that express an antisense Taura syndrome virus coat protein gene", 2005, Antiviral Res., vol. 67: pp. 141-146.*
Shekhar, M. et al., "Application of Nucleic-acid-based Therapeutics for Viral Infections in Shrimp Aquaculture", Mar. 2009, Biotechnol., vol. 11: pp. 1-9.*

* cited by examiner

*Primary Examiner* — Michael Burkhart
(74) *Attorney, Agent, or Firm* — Edwards Wildman Palmer LLP; Kathleen Williams

(57) ABSTRACT

An anti-WSSV and/or TSV nucleic acid drug, the active ingredients of which are five nucleic acids whose nucleotide sequences are sequence 1, sequence 2, sequence 3, sequence 4 and sequence 5 in the sequence list, respectively. The nucleic acid drug of the present invention has no toxic or side effect or drug tolerance, and can directly kill WSSV and/or TSV with fine antiviral effect and no drug residues.

3 Claims, No Drawings

SEQUENCE LISTING

<160> NUMBER OF SEQ ID NOS: 5

<210> SEQ ID NO 1
<211> LENGTH: 21
<212> TYPE: RNA
<213> ORGANISM: Unknown
<220> FEATURE:
<223> OTHER INFORMATION: an anti-WSSV and/or TSV ribonucleic acid
      sequence

<400> SEQUENCE: 1
ucagaaucgc uguccuucuu u                                              21

<210> SEQ ID NO 2
<211> LENGTH: 21
<212> TYPE: RNA
<213> ORGANISM: Unknown
<220> FEATURE:
<223> OTHER INFORMATION: an anti-WSSV and/or TSV ribonucleic acid
      sequence

<400> SEQUENCE: 2
agucacagga augcggaggu u                                              21

```
<210> SEQ ID NO 3
<211> LENGTH: 21
<212> TYPE: RNA
<213> ORGANISM: Unknown
<220> FEATURE:
<223> OTHER INFORMATION: an anti-WSSV and/or TSV ribonucleic acid
      sequence

<400> SEQUENCE: 3
auggucgcug ugcuaaguau u                                              21

<210> SEQ ID NO 4
<211> LENGTH: 21
<212> TYPE: RNA
<213> ORGANISM: Unknown
<220> FEATURE:
<223> OTHER INFORMATION: an anti-WSSV and/or TSV ribonucleic acid
      sequence

<400> SEQUENCE: 4
cacuaccaua agggagauau u                                              21

<210> SEQ ID NO 5
<211> LENGTH: 21
<212> TYPE: RNA
<213> ORGANISM: Unknown
<220> FEATURE:
<223> OTHER INFORMATION: an anti-WSSV and/or TSV ribonucleic acid
      sequence

<400> SEQUENCE: 5
ucuaauuuca gaauuucaau u                                              21
```

ANTI-WSSV AND/OR TSV NUCLEIC ACID DRUG

RELATED APPLICATIONS

This application is a continuation of PCT international application Ser. No. PCT/CN2011/077087, filed Jul. 12, 2011, designating the United States, which claims the benefit of Chinese Application No. 201010228664.5, filed Jul. 16, 2010. The entire contents of the aforementioned patent applications are incorporated herein by this reference.

TECHNICAL FIELD

The present invention relates to an anti-WSSV and/or TSV nucleic acid drug.

BACKGROUND ART

Large-scale prawn culture has been developed since 1970s-1980s. The coastal area of China, from south to north, has large output of prawn, and this promotes the growth of economy. Nowadays, virus infection poses a grave threat to prawn culture and leads to great economic losses of prawn culture farms. Taura Syndrome Virus (TSV) and White Spot Syndrome Virus (WSSV) infections are two major infectious diseases which seriously endanger the healthy development of prawn culture industry. According to a prawn disease report from the World Bank, viral diseases were responsible for 74% reduction of output in prawn culture and caused more than 3 billion dollars of economic losses all over the world in 1994. In 1995, these diseases were listed by OIE (International Office of Epizootics), FAO (Food and Agriculture Organization of the United Nations) and NACA (Network of Aquaculture Centre in Asia-Pacific) as one of the aquatic animal viral plagues that need to be reported.

WSSV infection was first found in Taiwan in 1992 and it broke out in prawn culture farms from south to north along the coast of Mainland China between May and August of 1993, and then it broke out in other Asian countries such as Japan. At present, WSSV infection has been reported to prevail in countries and regions including North Korea, Thailand, South Korea, Indonesia, Vietnam, Malaysia, India, Sri Lanka, Bangladesh, coastal areas of Mainland China and Taiwan, etc. In 1995, WSSV was found in prawn culture farms in Texas, U.S.A., and then prevailed in other regions of the western hemisphere. From then on, WSSV infection spreads worldwide and causes tens of billions of economic losses of prawn culture industry every year, and it becomes the major disease which threatens the prawn culture industry.

With the increase of market demands and improvement of rearing techniques, aquaculture industry has developed rapidly in China. However, as the requirements for quality become higher and higher in both domestic and overseas markets, safety barriers are gradually built for aquatic products in China because of drug residues exceeding standard from time to time, as well as the higher probability of carrying viruses, bacteria, parasites and biotoxins in the aquatic products. Prawns are invertebrates and resist to pathogenic invasions mainly through non-specific immunity including cellular and humoral immunities. These two immunities relate closely to each other, wherein humoral immunity factors are synthesized and released by blood cells, cellular immunoreactions in turn are mediated and affected by humoral immunity factors. Immunopotentiators are now mainly used to promote or induce defense reactions in host (prawns) and enhance the resistance against diseases. Therefore, although vaccination can achieve good results in vertebrates, it is especially important to develop a new method for treatment and prevention of prawn diseases in prawns.

Contents of the Invention

The present invention aims to provide a nucleic acid drug that can kill WSSV and/or TSV directly, and has good antiviral effects without toxic or side effects, drug tolerance, or drug residues.

The anti-WSSV and/or TSV nucleic acid drug provided by the invention has active components of 5 nucleic acids, the sequences of which are respectively SEQ ID NOs: 1, 2, 3, 4, and 5.

The anti-WSSV and/or TSV nucleic acid drug of the invention has any mass ratio of the 5 nucleic acids.

The anti-WSSV and/or TSV nucleic acid drug of the invention has a mass ratio of the 5 nucleic acids of 1:1:1:1:1.

The anti-WSSV and/or TSV nucleic acid drug of the invention also comprises pharmaceutically acceptable vectors or excipients.

The anti-WSSV and/or TSV nucleic acid drug of the invention can specifically kill WSSV and/or TSV directly, and has good antiviral effects without toxic or side-effect, drug tolerance, or drug residues. The nucleic acid drug can control WSSV and/or TSV infections in prawns and prevent massive deaths, therefore, reducing risks in prawn culture. Meanwhile, the present drug avoids the problem of drug residues exceeding standard caused by chemical drugs against viruses and bacteria, and improves quality of prawn products.

EMBODIMENTS

The following nucleic acids were synthesized artificially:

```
VP19-1:    5'- UCAGAAUCGCUGUCCUUCUUU -3';
VP19-2:    5'- GUCAUCAUCAUCGGUGACCUU -3';
VP19-3:    5'- CCUGGUCCUGUUCUUAUAUUU -3';
VP28-1:    5'- CGAUAUUGUCUGUGUGGGUUU -3';
VP28-2:    5'- AGUCACAGGAAUGCGGAGGUU -3';
VP28-3:    5'- UUUCCAUUGCGGAUCUUGAUU -3';
CP1-1:     5'- AUGGUCGCUGUGCUAAGUAUU -3';
CP1-2:     5'- AAUAUUUCCACGCCACCAAUU -3';
CP1-3:     5'- CACUACCAUAAGGGAGAUAUU -3';
CP2-1:     5'- UUGAGAACGGAAAUGACGAUU -3';
CP2-2:     5'- CUUUAGCAAGCGUACCUGGUU -3';
CP2-3:     5'- UCUAAUUUCAGAAUUUCAAUU -3'.
```

Experimental conditions: Experiments were carried out in small water tanks, at the temperature of 20±2° C.;

Experimental animals: *Penaeus japonicus* Bate, with about 10 g body weight for each, and a body length of 10-12 cm;

Virus strains: WSSV, TSV;

Preparation of virus suspension: 10 g of pathological prawn of disease was homogenized in 500 mL of TNE buffer, and centrifuged at 4° C., 3500×g for 5 min. The resulted supernatant was filtrated by a 400 mesh nylon net, then centrifuged at 4° C., 30000×g for 30 min, and the resulted supernatant was discarded. The precipitate was resuspended in 10 mL of TM buffer, and subjected to centrifugation at 3500×g for 5 min, then centrifuged at 4° C., 30000×g for 20 min. Virus particles from the precipitate were resuspended in 1 mL of TM buffer and subjected to quantitative analysis by PCR. The resulted virus suspension was then adjusted to a proper concentration by nomal saline.

WSSV infection: The virus was injected into the second to last urite from the tail of prawn; for the group with infection but no drug administration, 100 μL of WSSV suspension was injected into each prawn; for the blank control group, same amount of 0.9% sterile nomal saline was injected into each prawn; for the group with both infection and drug administration, WSSV suspension was injected, and 0.2 mg/day/prawn of the nucleic acid of present invention was mixed into feed and administrated. Prawn activities, disease symptoms and deaths, such as distinct white spots inside the carapace and rapid decrease of activities, etc., were observed after injection every day, and the observation was continued for 10 days; 30% of water was refreshed and prawns were fed once at dusk every day.

TSV infection: TSV infection was performed in the same way as WSSV.

WSSV was assayed as follows:

(1) DNA extraction by boiling method: 0.1 g of muscle tissue was taken from WSSV-infected prawn and subpackaged into a 1.5 ml centrifugal tube, wherein 1 ml of PBS buffer (pH 7.4) was added to each tube, followed by homogenizing in an ice-bath. The homogenate liquid was centrifuged in 6000 rpm for 5 min. 50 μl of the resulted supernatant was taken and added with 1 μl of Protease K (10 mg/mL), then subjected to boiling at 55° C. for 15 min; next, ice-cooled instantly for 5 min, and centrifuged at 8000 rpm for 10 min. The resulted supernatant was used as PCR template.

(2) Primers

Primers for the First Amplification:

```
F1:  5'- CGT GCC TGA ATC A GT ATG TAC GC- 3';

R1:  5'- GAC GTT ACA ATA GAC CCA TGT TCG AT-3';
```

Primers for the Second Amplification:

```
F2:  5'- CTC ATG TAC CAA ATC TGG GTT ACG A-3',

R2:  5'-CGA TAG ACC ACA A GT TCC GTA GGA-3'.
```

(3) PCR system and procedure for WSSV assay:

(i) PCR system:

The first amplification: 2.5 μL 10×PCR buffer, 0.4 μL dNTP (2.5 mM), 0.8 μL primers (F1+R1), 0.3 μL TaqDNA polymerase (5 U/μL), and 2.0 μL template DNA; and supplemented with 19 μL ddH$_2$O;

The second amplification: 2.5 μL 10×PCR buffer, 0.4 μL dNTP (2.5 mM), 0.8 μL primers (F2+R2), 0.3 μL Taq DNA polymerase (5 U/μL), and 2.0 μL DNA product from the first amplification; supplemented with 19 μL ddH$_2$O.

(ii) PCR amplification procedure: 95° C., 2 min; 35 cycles of: 95° C., 30 s; 55° C., 30 s, and 72° C., 1 min; and finally, 72° C., 10 min, followed by preserving at 10° C.

(4) 1% agarose gel electrophoresis was performed after PCR.

DNA product from the first amplification had a fragment length of about 328 bp, and that from the second amplification was about 258 bp.

TSV was Assayed as Follows:

Amplification system (20 μL): Real-time PCR Premix 10 μL, 25 mmol/L MgCl$_2$ 0.25 μL, 2.5 mmol/L dNTP 0.5 μL, 5 U/μL Taq DNA polymerase 0.125 μL, and 2 μL of each of Tsv-F, Tsv-R, and Tsv-T, with concentrations of 0.6, 0.4, and 0.6 μmol/L, respectively; supplemented with H$_2$O.

PCR amplification procedure: pre-denaturing at 95° C. for 20 s; 40 cycles of denaturing at 95° C. for 10 s, annealing and extending at 60° C. for 30 s; followed by terminating the reaction at 40° C.

Finally, the data was analyzed with software.

```
Tsv-F:  5'-GCTTGCGTGGTGGGACTAAAT -3';

Tsv-R:  5'-CCTCCACTGGTTGTTGTATCAAAA-3';

Tsv-T:  5'-HEX-AATGCCTGCTAACCCAGTCGAAATT -
        ECLIPSE-3'.
```

The analysis results of anti-WSSV activities of nucleic acids for prawns were shown in Table 1;

The analysis results of anti-TSV activities of nucleic acids for prawns were shown in Table 2.

TABLE 1

Anti-WSSV activities of nucleic acids for prawns

| NOs. | Treatments | PCR positive rates | Protective rates |
|---|---|---|---|
| 1 | VP19-1 | 20% | 80% |
| 2 | VP19-2 | 12% | 88% |
| 3 | VP19-3 | 27% | 73% |
| 4 | VP28-1 | 36% | 64% |
| 5 | VP28-2 | 9% | 91% |
| 6 | VP28-3 | 43% | 57% |
| 7 | Positive control | 100% | 0 |
| 8 | Negative control | 0 | — |

TABLE 2

Anti-TSV activities of nucleic acids for prawns

| NOs. | Treatments | PCR positive rate | Protective rate |
|---|---|---|---|
| 1 | CP1-1 | 14% | 86% |
| 2 | CP1-2 | 34% | 66% |
| 3 | CP1-3 | 19% | 81% |
| 4 | CP2-1 | 41% | 59% |
| 5 | CP2-2 | 11% | 89% |
| 6 | CP2-3 | 9% | 91% |
| 7 | Positive control | 100% | 0 |
| 8 | Negative control | 0 | — |

As shown in Tables 1 and 2, VP19-1, VP19-2, VP28-2, CP1-1, CP1-3, CP2-2 and CP2-3 exhibited higher activities against WSSV and TSV.

A nucleic acid drug was then prepared by mixing VP19-1, VP28-2, CP1-1, CP2-3 and CP2-3 with mass ratio of 1:1:1:1:1.

Stability analysis of the nucleic acid drug: the bioactivity of the nucleic acid drug was not affected under the following conditions: 20 min of circulating steam (sterilization) at high temperature of 105° C.; storage in oven at constant temperature of 50° C. for 2 months; storage at room temperature for 24 months; or storage at −20° C. for 48 months.

Penaeus japonicus Bate, about 10 g for each prawn with a body length of 10-12 cm were divided randomly into 14 groups, 100 for each group, and then each group was intramuscularly injected with VP19-1, VP19-2, VP19-3, VP28-1, VP28-2, VP28-3, CP1-1, CP1-2, CP1-3, CP2-1, CP2-2, CP2-3, the nucleic acid drug, and 0.9% sterile saline, respectively. Activities and deaths were observed every day after injection, and the result was shown in Table 3.

TABLE 3

Toxicity analysis for prawns

| NOs. | Treatments | Survival rates |
|---|---|---|
| 1 | VP19-1 | 92% |
| 2 | VP19-2 | 96% |
| 3 | VP19-3 | 95% |
| 4 | VP28-1 | 99% |
| 5 | VP28-2 | 97% |
| 6 | VP28-3 | 100% |
| 7 | Nucleic acid drug | 99% |
| 8 | 0.9% sterile saline | 100% |
| 9 | CP1-1 | 93% |
| 10 | CP1-2 | 96% |
| 11 | CP1-3 | 97% |
| 12 | CP2-1 | 92% |
| 13 | CP2-2 | 100% |
| 14 | CP2-3 | 100% |

Clinic Trials

Preparation of virus filtrates: gills, epithelia, muscles, ambulatory legs and head soft tissues were respectively taken from WSSV and TSV infected prawns to be homogenized in PBS buffer (pH7.14), followed by centrifugation at 8000×g for 10 min in order to remove precipitate. The supernatant was filtrated with a 0.45 μm membrane to obtain virus filtrates of WSSV and TSV for inducing infection.

Feed infection: The above virus filtrates of WSSV and TSV were respectively injected into healthy prawns, and the resulted prawns that were about to die were collected and preserved at −20° C. to serve as sick prawns for feed infection. For infection, gills, epithelia, muscles, ambulatory legs and heads were taken from said prawns and cutted into meat paste, then the meat paste subjected to penicillin and streptomycin treatment for 0.5 h. After fasting for 24 h, juvenile prawns in challenge group were fed once with the above meat paste of the sick prawns; and after 6 h, residues were cleaned, followed by feeding corresponding bait respectively. Meanwhile, negative control group was established.

Drug administration approach: The nucleic acid drug was mixed into prawn feed at 200 mg/kg and administrated by feeding.

Symptom observation: After infection, activities and deaths were observed every day, and some prawns were selected randomly after 10 days to perform virus assay, the same procedures as above-mentioned WSSV and TSV assay were followed.

The statistical data were shown in Tables 4 and 5.

TABLE 4

Resistance to WSSV

| NOs. | Treatments | PCR positive rates | Survival rates |
|---|---|---|---|
| 1 | Nucleic acid drug | 3% | 98% |
| 2 | Positive control | 97% | 51% |
| 2 | Negative control | 0 | 99% |

TABLE 5

Resistance to TSV

| NOs. | Treatments | PCR positive rates | Survival rates |
|---|---|---|---|
| 1 | Nucleic acid drug | 4% | 97% |
| 2 | Positive control | 91% | 57% |
| 2 | Negative control | 0 | 95% |

The above examples only aim to describe the best modes of the present invention and the scopes of the present invention are not limited within them. Without departing from concepts of the present invention, all kinds of changes and modifications on the technical solution of the present invention, made by a person skilled in the art, should be within the protection scopes defined by the claims.

The invention claimed is:

1. An anti-WSSV and/or TSV nucleic acid drug comprising 5 nucleic acids as active components, wherein the sequences of said 5 nucleic acids are SEQ ID NOs: 1, 2, 3, 4, and 5, respectively.

2. The nucleic acid drug according to claim 1 having a mass ratio of the 5 nucleic acids as 1:1:1:1:1.

3. The nucleic acid drug according to claim 2, further comprises pharmaceutically acceptable vectors or excipients.

* * * * *